United States Patent [19]

Risser et al.

[11] Patent Number: 5,244,656
[45] Date of Patent: Sep. 14, 1993

[54] ANTIGEN SPECIFIC PLASMACYTOMAS AND ANTIBODIES DERIVED THEREFROM

[75] Inventors: Rex G. Risser; David A. Largaespada, both of Madison, Wis.; Joseph F. Mushinski, Bethesda, Md.; Eva M. Weissinger; Harald Mishak, both of Germantown, Md.

[73] Assignees: Wisconsin Alumni Research Foundation, Madison, Wis.; The United States of America as represented by the Department of Health and Human Services, Washington, D.C.

[21] Appl. No.: 762,169

[22] Filed: Sep. 19, 1991

Related U.S. Application Data

[63] Continuation of Ser. No. 518,887, May 4, 1990, abandoned.

[51] Int. Cl.$^5$ ............ C12N 5/00; C12N 15/00; A61K 39/00
[52] U.S. Cl. ............ 424/88; 435/240.2; 435/172.3; 424/89; 530/387.1; 935/57
[58] Field of Search ............ 435/240.2; 424/88, 89; 530/387, 387.1; 935/57

[56] References Cited

U.S. PATENT DOCUMENTS 4,736,866  4/1988  Leder et al.
4,997,764  3/1991  Favera.

FOREIGN PATENT DOCUMENTS

WO8603780  7/1986  European Pat. Off.

OTHER PUBLICATIONS

Hartmann et al. Mol Immunol. 26(4): 359, 1989.
Clynes et al. PNAS 85: 6067, 1988.
Rosenbaum et al. pp. 897-906, 1989.
Green et al. J. of Virol. 61: 2192, 1987.
Casali et al. Science 234: 476, 1986.
Potter, Surv. Synth. Path. Res. 3: 499, 1984.
Potter, Seminars in Oncology 13(3): 275, 1986.
P. Green et al., 61 J. Virol. 2192-2197 (1987) (A--MuLV).
W. Stanton et al., 303 Nature 401-406 (1983) (c-myc).
S. Cory et al., 1 Oncogene Res. 61-76 (1987) (pDOL-myc).
R. Mann et al., 33 Cell 153-159 (1983) (psi-2).
A. Hartman et al., 26 Mol. Imun. 359-370 (1989) (immunoassay).
M. Jolley et al., 67 J. Immunol. 21-35 (1984) (immunoassay).
H. Rosenbaum et al., An E$\mu$-v-abl Transgene Elicits Plasmacytomas In Concert With An Activated myc gene, 897-906 (1989).
W. Huse et al., 246 Science 1275-1276 (1989).
H. Bialy et al., 8 Bio/Technology 184 (1990).
P. Green et al., 84 P.N.A.S. USA 5932-5936 (1987) (general).

Primary Examiner—Elizabeth C. Weimar
Assistant Examiner—Suzanne Ziska
Attorney, Agent, or Firm—Quarles & Brady

[57] ABSTRACT

Disclosed herein is a method for producing antibodies against an antigen of interest. Animal cells are exposed to both the antigen of interest and a recombinant retroviral vector. The vector contains a combination of oncogenes capable of inducing plasmacytomas. Plasmacytoma formation takes place rapidly and takes place in the presence of the antigen. A very high proportion of the plasmacytomas that are recovered are antigen specific.

1 Claim, 1 Drawing Sheet

ANTIGEN SPECIFIC PLASMACYTOMAS AND ANTIBODIES DERIVED THEREFROM

This application is a continuation of application Ser. No. 07/518,887, filed May 4, 1990, abandoned.

This invention relates to a method for producing antibodies that selectively bind to an antigen of interest. It involves using a combination of activated oncogenes and the antigen of interest to help select plasmacytomas during their formation.

BACKGROUND OF THE INVENTION

The method of choice for creating monoclonal antibodies has since 1975 been the Kohler-Milstein technique. This technique involved fusing together an established cell line from a mouse tumor with spleen cells from a mouse. The mouse had previously been immunized with the antigen. It was then necessary to select hybrid cells that survived and screen numerous individual cultures in order to find a hybridoma that made the desired antibody.

"Hybridoma" technology, although a major advance, has significant disadvantages. Because the hybrid cells have extra chromosomes, they are sometimes unstable and lost during culture. Thus, many cultures must be screened to be sure of finding surviving cultures. Further, one often has to culture hybridomas for several months before being sure that a stable clone has been recovered. Further, the screening techniques are frequently burdensome and time consuming.

Another newer technique for antibody development is described in W. Huse et al., 246 Science 1275-1281 (1989). In this technique, a bacteria phage lambda vector system is used to express in *E. coli* a combinatorial library of antibody fragments of mouse antibody repertoire (in vitro). This system still appears to require significant screening. Also, it has been criticized as being so burdensome that further development will be needed to make it practical. H. Bialy, 8 Biotechnology 184 (1990).

Thus, it can be seen that a need still exists for an improved means of developing antibodies.

SUMMARY OF THE INVENTION

In one aspect, the invention provides a method for producing antibodies against an antigen of interest. One exposes animal cells to the antigen and also exposes the cells to a recombinant vector capable of inducing plasmacytomas. Because of the presence of both the antigen and the vector, plasmacytomas are selectively produced and can produce antibody to the antigen. "Plasmacytomas" as used herein are tumors of immunoglobulin secreting cells (e.g. tumors of plasma cells). Preferably, live animals (such as a mouse or rabbit) or cells from the animal (e.g. peripheral blood cells) are exposed to the vector after the animal has already developed antibodies to the antigen (by pre-immunizing the animal with the antigen).

Antigens that have already been tested include hen egg lysozyme ("HEL") and sheep red blood cells ("SRBC"). However, it will be appreciated from the discussion below that the invention is intended to work with a wide range of antigens. Also, the invention can be adapted to work in a wide range of organisms.

A highly preferred vector is a retrovirus that carries multiple different oncogenes. It has been discovered that in combination, oncogenes c-myc and v-abl have a synergistic effect in their ability to induce plasmacytomas. They have even greater ability to induce plasmacytomas in mice in the presence of mineral oil such as pristane. The combination of c-myc and v-ras (or c-myc and v-raf) have plasmacytoma inducing capability in the presence of pristane. Note that numerous other oncogenes have been found. See e.g. K. Burck et al., Oncogenes: An Introduction To The Concept Of Cancer Genes (Springer-Verlag 1988). Many other oncogenes are expected to be found as well.

In another aspect, the invention provides cell lines that are directly or indirectly "derived using" the plasmacytomas developed by the above method.

In yet another aspect, the invention provides antibodies that are directly or indirectly "derived using" the above cell lines.

It will be appreciated that it has been discovered that when one exposes an animal (or animal cell culture containing B or pre-B cells) to both a vector suitable to induce plasmacytoma formation and the antigen of interest, the animal (or culture) itself facilitates growth on a selective basis of the plasmacytomas that produce antibody to the antigen. One can then take the plasmacytomas and use them to establish tumors lines in animals or cell lines in tissue culture.

The objects of the invention therefore include providing:

a method of the above kind for providing antibodies against a specific antigen;

a method of the above kind which can be performed either in vivo with minimal screening or in vitro;

a method of the above kind which is relatively rapid and reduces the time needed to develop immortalized antibody producing cell lines; and antibodies and cell lines produced from the above methods.

These and still other objects and advantages of the present invention will be apparent from the description which follows. The following embodiments do not represent the full scope of the invention. Rather, the invention may be employed in other embodiments. Reference is therefore to be made to the claims herein for interpreting the scope of the present invention.

DESCRIPTION OF THE PREFERRED EMBODIMENTS

Figure 1:
FIG. 1 shows a preferred vector of the present invention.

To construct the preferred "abl/myc" vector of FIG. 1, we inserted a c-myc gene under the control of the herpes simplex virus thymidine kinase promoter (tkpro) into a proviral clone of Abelson murine leukemia virus ("A-MuLV") (pABpro). See generally P. Green et al., 61 J. Virol 2192-2197 (1987) (source of A-MuLV). The c-myc gene is a cDNA from a plasmacytoma induced in a BALB/c mouse and contains the entire c-myc coding sequence from a XhoI site in exon I to another XhoI site in exon III. See W. Stanton et al., 303 Nature 401-406 (1983). BamHI linkers were added to the ends of the blunted XhoI fragment and cloned into the vector pDol. See S. Cory et al., 7 Oncogene Research 61-76 (1987) (source of pDOLmyc). This BamHI c-myc fragment was removed from pDOL and the fragment was ligated to a SmaI to BglII tkpro fragment which were inserted together into pUC19 cut with HincII and BamHI. This created an intermediate construct called ptk-myc. Plasmid ptk-myc was cut with BamHI and HindIII which produces a tk-promoter-c-myc fragment. This was ligated to pABpro cut with HindIII and BamHI to produce pABL-MYC. A one liter culture of E. coli strain JM107 containing pABL-MYC was grown and plasmid purified by twice CsCl$_2$ banding. The myc gene in ABL-MYC virus is thus transcribed as part of a viral genome and from the internal tk promoter.

To produce pools of the virus, pABL-MYC was transfected into the packaging cell line psi-2 (see R. Mann et al. 33 Cell 153-159 (1983) or A.T.C.C.) or with pMOV-3 (R. Jaenish, Whitehead Institute, Cambridge Mass.) cotransfected into NIH-3T3 (A.T.C.C.) cells to produce helper-free or helper-containing virus pools respectively. The transfections were done by the CaPO$_4$ coprecipitation method. Foci of transformed cells appeared in 12-14 days. These foci were picked and passaged until free of non-transformed flat cells by harvesting loosely attached cells. Tissue culture supernatant was harvested from semi-confluent 100 mm plates after 24 hour incubations in 5% CS DMEM. The supernatant was centrifuged three times at 2000 RPM and frozen in aliquots at $-70°$ C. The titer of ABL-MYC virus was determined by focus formation on NIH-3T3 cells. The titer of replication-competent Moloney murine leukemia virus ("M-MuLV") was determined by the UV-XC plaque assay on NIH-3T3 cells.

Helper-free ABL-MYC was prepared by transfection of the psi-2 packaging cells and recovery of transformed cell clones. See generally P. Green et al., 84 P.N.A.S. USA 5932-36 (1987). Viruses were titered on NIH3T3 cells by focus formation and colony formation in agarose suspension. The focus-forming titers of A-MuLV and ABL-MYC were comparable, however ABL-MYC was 10-fold more efficient at inducing agarose colonies. These results suggest that ABL-MYC virus is more efficient at some aspects of transformation than A-MuLV.

ABL-MYC-transformed NIH3T3 cells were also examined for the presence of proviral sequences and for expression of viral RNA. The predicted proviral structure was found, and no rearrangement of the endogenous c-myc locus was detected. Myc RNA that comigrate with viral U3 sequences was detected.

To confirm the activity of the ABL-MYC in vivo we inoculated mice intravenously with helper-containing or helper-free virus pools. ABL-MYC virus induced a high incidence of lymphomas in mice normally susceptible to A-MuLV disease. The latent period for tumor development was approximately 30-40 days, a result typical of A-MuLV disease. Gross and microscopic pathology of diseased mice was usually indistinguishable from that of A-MuLV. ABL-MYC tumors were oligoclonal in origin because they showed only a few proviral integration sites. Examination of the Ig loci in these tumors indicated that Jh rearrangement had taken place, however no rearrangement of the kappa light chain locus was detected. These results suggest that these ABL-MYC tumors are of pre-B cell origin.

In mice resistant to A-MuLV lymphomagenesis, a different pattern of pathology was seen with ABL-MYC virus. A high percentage of the mice developed plasmacytomas with a median latent period of 80-90 days. The tumors appeared as masses in the mesenteries of the gut and were frequently found growing out of the intestinal wall. Microscopic analysis confirmed that the major cell type in these tumors was a plasma cell. Cells showed large amounts of cytoplasm, acentric nuclei and clear perinuclear spaces. Frequently, mice also developed ascites cell growth. Examination of the sera or ascites fluid of the mice indicated that each contained an unusually high titer of a single class of immunoglobulin ("Ig"). Of 18 samples examined, 12 contained high levels of IgA, 4 contained high levels of IgM, 1 contained IgG, and 1 contained IgA and IgM. Also, if mice normally susceptible to A-MuLV were injected intraperitoneally with pristane followed 20 days later with ABL-MYC virus, a high incidence of plasmacytomas developed 20-40 days thereafter. Therefore, we concluded that if ABL-MYC-infected mice do not develop pre-B cell tumors, under this vector challenge they usually go on to develop plasmacytomas, even in the absence of priming (albeit priming will expedite plasmacytoma formation).

Initial attempts to culture plasmacytomas in vitro failed until supernatant from P388 tumor cells was included in the culture medium. Examination of the DNA of the plasmacytomas indicated that they contained the expected ABL-MYC provirus and did not show any rearrangement of the endogenous c-myc locus. Plasmacytomas were of clonal origin as judged by the pattern of kappa gene rearrangement.

Antigen Immunization

We followed the following procedure:
(a) Day 1: Immunization of five Balb/c mice with 50 ug hen egg white lysozyme in complete Freund's Adjuvant (50 ug HEL/mouse)
(b) Day 14: Immunization of five Balb/c mice with 50 ug additional HEL (per mouse) in incomplete Freund's adjuvant
(c) Day 16: Infection of immunized animals with $2 \times 10^5$ ffu/ mouse ABL-MYC retrovirus
(d) Day 28: third immunization with HEL (30 ug HEL in PBS/mouse)

Mouse 1 developed severe ascites and had several tumors in the mesentery. Ig-typing showed that the secreted antibody was an IgA with k light chain. Mouse 2 had several tumors in the mesentery. Ig-typing showed that it secreted IgA and IgM antibodies with kappa light chains. Mouse 3 had two tumors in the mesentery and both secreted IgA. Mouse 4 developed several tumors and ascites contained an IgM antibody with a k light chain. Mouse 5 had seven tumors in the mesentery.

We obtained smears from ascites tumor cells from all five animals and found plasmacytoma cells in all five. We then transplanted the tumors by injecting cells from the ascites fluid from the five mice into five pristane primed Balb/c mice. All developed further tumors. Also, some of the tumors from mouse 3 and mouse 5 were minced and injected into ten mice. Two of these mice have already developed plasmacytomas.

Other Antigens

Similar experiments were then conducted with SRBC as the antigen as follows: BALB/c mice 60 days of age received 0.25 ml of 10% sheep red blood cells in phosphate buffered medium by intraperitoneal (IP) injection. Seven days later, the mice were injected IP with 0.5 ml pristane (to produce an environment for optimal growth of plasmacytomas). Seven days later the mice received another SRBC injection (0.25 ml 10% SRBC). Two days later the mice were injected with 0.5 ml of ABL-MYC virus IP ($3.5 \times 10^5$ focus-forming units of virus). Two weeks later, the mice were injected with 0.25 ml of 10% SRBC IP. Plasmacytomas developed within a month of the virus injection.

In Vitro

While the experiments above dealt with in vivo application, the invention also has utility in vitro. In this regard, BALB/c mice were immunized with 0.25 ml SRBC as before and injected with pristane. Spleens were then removed from the mice prior to retrovirus infection. Single cell suspensions of spleen cells were prepared. Cells (at $4 \times 10^6$ ml) were infected (at $1-3 \times 10^5$ ffu/ml) in vitro with a) ABL-MYC (M-MuLV); b) ABL-MYC (psi 2); or c) M-MuLV (control virus). Cells were plated at $5 \times 10^5$ cells/ml in mass culture or at $10^{4/.1}$ ml in microtiter plates.

Cells cultures were fed at regular intervals ±SRBC. At 14–21 days post-infection cultures were examined for the presence of continuously growing cells and 50 ul of culture supernatant (diluted) was tested for its ability to react with SRBC as specified below.

Test For Anti-Hel Activity

The panel of test antigens was as follows: HEL (hen egg white lysozyme), HUL (human milk lysozyme), SN (micrococcal nuclease), L.C. (mouse lens crystallin), MSA (mouse serum albumin), BSA (bovine serum albumin), Phosphocholine, TNP (Trinitrophenol), ghum gatti (galactan), IgGl (mouse IgG, similar to human rheuma factor), POL (bacterial flagellin) and Inulin. Ascites fluid was taken from the mice, diluted to $10^{-4}$, and screened for reactivity against the test panel using a particle concentration fluorescence immunoassay of the type described in A. Hartman, et al., 26 Mol. Immun. 359–370 (1989); M. Jolley et al., 67 J. Immunol. 21–35 (1984).

Five tumors were tested, and all tested positive only against HEL. The tumors were transplanted to five pristane-primed mice which had never been immunized. Tumors developed from three of the transplants (and ascites fluid from each was highly reactive with only HEL).

Reactivity for SRBC was characterized by three standard methods: 1) hemagglutination 2) direct and indirect plague-forming cell assay and 3) direct binding of antibody to lysates of SRBC adsorbed to microtiter plates followed by binding heavy chain class-specific antibodies and detection by ELISA (see E. Harlow et al., Antibodies, A Laboratory Manual, Cold Spring Harbor Laboratory (1988). Serum or ascites tumor cells or ascites fluid from mice that developed tumors following injection of SRBC and ABL-MYC virus were tested. Sixteen showed reactivity for SRBC in one or more assays and one tumorous mouse showed no anti-SRBC activity. In nine mice, a high proportion of plasma cells in ascites fluid formed direct plagues with SRBC, and each mouse contained a high titer of IgM reactive for SRBC as expected. One mouse contained a high proportion of indirect plague-forming plasma cells and a high titer of $IgG_{2b}$ reactive with SRBC. Three mice contained high titers of circulating IgA reactive for SRBC in ELISA assays, and three contained high titers of anti-SRBC $IgG_{2b}$ in ELISA assays. Control immunized uninfected mice contained undetectable quantities of anti-SRBC IgA or $IgG_{2b}$ at the dilution of serum or ascites fluid (1/1000) used to test tumor-bearing mice.

For experiments that involved in vitro infection of spleen cells from mice immunized with SRBC, only the hemagglutination assay was used. Supernatants were harvested from cultures 14 day post-infection and tested at ⅛ dilution. Of three cultures infected with ABL-MYC (psi 2), one showed hemagglutinating antibodies. Of five cultures infected with ABL-MYC/M-MuLV, none showed hemagglutinating antibodies. Of three cultures infected with M-MuLV helper control virus, none showed hemagglutinating antibodies. None of three cultures from infected non-immunized cells showed anti-SRBC antibody.

This testing of HEL and SRBC establishes that a very high percentage of the tumors formed are secreting antibodies specific for the immunizing antigen, and that the method works both in vitro and in vivo. The reactive antibody is of a single heavy chain class establishing the monoclonality of the antibody.

It will be appreciated from the above that the method permits the plasmacytomas to develop within two months. In the in vivo method, the tumors are pre-screened. Thus, months can be saved by using this technique. Also, with either in vitro or in vivo (and unlike hybrid cells), the tissue cultures are stable.

It is clear that both the antigen and the vector facilitate the result. However, it preferred that the host be immunized prior to infection to optimize screening.

To modify the method to other animal systems, one skilled in the art would appreciate that the controlling sequences on the virus (e.g. LTR) could be changed to those which are efficient in the selected animal's cells. In rabbit cells, an M-MuLV may be adequate without change. In human cells, an HIV-based expression vector may work best (including tat and rev genes). Alternatively, other expression vectors that are not virus based may be introduced to create the same effect.

It will also be appreciated that one might use an SCID/hu mouse that makes human antibodies. The mouse might be infected with amphotropic pseudotypes of abl/myc. In this regard, one might use the EBV oriP and EBNA protein for expression of v-abl and c-myc. Alternatively, SV-40 vector system or HIV-based vector systems can be used.

Another factor would be the viral envelope. For transmission of abl/myc retroviruses to non-murine cells, the envelope protein could be changed to that of amphotropic MuLV which has a broader host range (i.e. it will infect rabbit, human cells), or the envelope protein can be that of the selected host. In each case, the optimal growth factor for each species will have to be selected (e.g. IL-1, IL-6, IL-3).

Note also that various levels of in vitro procedure can be involved. One can perform all steps in vitro, or as described above one might use cells that have been immunized in vivo to further the in vitro method.

The primary use for the invention (from the industrial applicability standpoint) is to quickly create monoclonal antibodies. Such antibodies are, of course, themselves useful for diagnostic and pharmaceutical work. They may also have potential therapeutic value or other utility.

It will be appreciated that what has been discussed above are the preferred embodiments of invention. However, the invention also appears useful in other embodiments. Thus, the invention is not to be limited to the particular preferred embodiments above. The claims which follow should therefore be looked to determine the full scope of the claims.

We claim:

1. A method for in vivo production of antibodies against a specified antigen, comprising:
   immunizing a murine host with an exogenous antigen;
   injecting said host with pristane 7 days after the primary immunization in order to prime said host;
   immunizing said pristine-primed murine host with said exogenous antigen 7 days after injection of the pristane;
   two days after said second immunizing step, injecting said pristane-primed murine host with a recombinant retroviral vector that contains the c-myc and v-abl oncogenes so as to induce the production of plasmacytomas that produce antibodies against said exogenous antigen;
   twelve to fourteen days after the injection of the retroviral vector, immunizing said pristane-primed murine host with said exogenous antigen; and
   recovering ascites fluid from the peritoneal cavity of said immunized, pristane-primed murine host, said ascites fluid containing antibodies specifically reactive with said antigen, wherein each immunization and injection is intraperitoneal.

* * * * *